United States Patent
Lensing et al.

(10) Patent No.: US 6,458,610 B1
(45) Date of Patent: Oct. 1, 2002

(54) METHOD AND APPARATUS FOR OPTICAL FILM STACK FAULT DETECTION

(75) Inventors: Kevin R. Lensing; Marilyn I. Wright; James B. Stirton, all of Austin, TX (US)

(73) Assignee: Advanced Micro Devices, Inc., Austin, TX (US)

(*) Notice: Subject to any disclaimer, the term of this patent is extended or adjusted under 35 U.S.C. 154(b) by 0 days.

(21) Appl. No.: 09/871,015

(22) Filed: May 31, 2001

(51) Int. Cl.[7] .......................... G01R 31/26; H01L 21/66
(52) U.S. Cl. .............................. 438/16; 716/4
(58) Field of Search ................... 438/7, 16, 89, 438/14; 716/4, 5–6; 356/451–456

(56) References Cited

U.S. PATENT DOCUMENTS 6,304,999 B1 * 10/2001 Toprac et al. .................. 716/17

* cited by examiner

Primary Examiner—Craig Thompson
(74) Attorney, Agent, or Firm—Williams, Morgan & Amerson

(57) ABSTRACT

A method and an apparatus for performing film stack fault detection. At least one semiconductor wafer is processed. Metrology data from the processed semiconductor wafer is acquired. Data from a reference library comprising optical data relating to a film stack on the semiconductor wafer is accessed. The metrology data is compared to data from the reference library. A fault-detection analysis is performed in response to the comparison of the metrology data and the reference library data.

43 Claims, 9 Drawing Sheets

METHOD AND APPARATUS FOR OPTICAL FILM STACK FAULT DETECTION

BACKGROUND OF THE INVENTION

1. Field of the Invention

This invention relates generally to semiconductor manufacturing, and, more particularly, to a method and apparatus for performing film stack fault detection using optical data.

2. Description of the Related Art

The technology explosion in the manufacturing industry has resulted in many new and innovative manufacturing processes. Today's manufacturing processes, particularly semiconductor manufacturing processes, call for a large number of important steps. These process steps are usually vital, and therefore, require a number of inputs that are generally fine-tuned to maintain proper manufacturing control.

The manufacture of semiconductor devices requires a number of discrete process steps to create a packaged semiconductor device from raw semiconductor material. The various processes, from the initial growth of the semiconductor material, the slicing of the semiconductor crystal into individual wafers, the fabrication stages (etching, doping, ion implanting, or the like), to the packaging and final testing of the completed device, are so different from one another and specialized that the processes may be performed in different manufacturing locations that contain different control schemes.

Generally, a set of processing steps is performed on a group of semiconductor wafers, sometimes referred to as a lot, using a semiconductor manufacturing tool called an exposure tool or a stepper. Typically, an etch process is then performed on the semiconductor wafers to shape objects on the semiconductor wafer, such as poly-lines, which are conductive lines that connect one conductive region on the semiconductor region to another. The manufacturing tools communicate with a manufacturing framework or a network of processing modules. Each manufacturing tool is generally connected to an equipment interface. The equipment interface is connected to a machine interface to which a manufacturing network is connected, thereby facilitating communications between the manufacturing tool and the manufacturing framework. The machine interface can generally be part of an advanced process control (APC) system. The APC system initiates a control script, which can be a software program that automatically retrieves the data needed to execute a manufacturing process.

FIG. 1 illustrates a typical semiconductor wafer 105. The wafer 105 typically includes a plurality of individual semiconductor die arranged in a grid 150. Photolithography steps are typically performed by a stepper on approximately one to four die locations at a time, depending on the specific photomask employed. Photolithography steps are generally performed to form patterned layers of photoresist above one or more process layers that are to be patterned. The patterned photoresist layer can be used as a mask during etching processes, wet or dry, performed on the underlying layer or layers of material, e.g., a layer of polysilicon, metal or insulating material, to transfer the desired pattern to the underlying layer. The patterned layer of photoresist is comprised of a plurality of features, e.g., line-type features, such as a polysilicon line, or opening-type features, that are to be replicated in an underlying process layer. Using the processes described above, a plurality of film layers are stacked to create a film stack, which leads to the production of integrated circuits on a semiconductor wafer.

Generally, a plurality of layers is formed on a semiconductor wafer using various materials such as polysilicon material, insulating material such as silicon dioxide, and the like. Ultimately, features of semiconductor devices will be formed in these layers using known photolithography and etch processes. In order to create various features of a semiconductor device, such as a transistor, a plurality of film stacks are formed. For example, a gate electrode may be patterned from a film stack comprised of a layer of polysilicon formed above a gate insulation layer that is formed above a silicon substrate. Another example of a film stack may comprise a layer of polysilicon and a layer of silicon oxynitride stacked on a silicon substrate.

Due to the complexities of manufacturing facilities, tracking the characteristics of film stacks may be difficult. A particular film stack may be sent through various processing steps. At the same time, a different film stack may also be processed by the same manufacturing facility. It is important that an accurate characterization of the film stack is available before a particular process, such as an etch process, is performed on the film process. Using current methodology, generally, film stacks are characterized by the thickness of the films in the film stack. Using this characterization, fault detection is performed on the semiconductor wafers being processed. However, without an accurate characterization of the film stack, an efficient fault detection analysis is difficult.

The present invention is directed to overcoming, or at least reducing the effects of, one or more of the problems set forth above.

SUMMARY OF THE INVENTION

In one aspect of the present invention, a method is provided for performing film stack fault detection. At least one semiconductor wafer is processed. Metrology data from the processed semiconductor wafer is acquired. Data from a reference library comprising optical data relating to a film stack on the semiconductor wafer is accessed. The metrology data is compared to data from the reference library. A fault-detection analysis is performed in response to the comparison of the metrology data and the reference library data.

In another aspect of the present invention, a system is provided for performing film stack fault detection. The system of the present invention comprises: a computer system; a manufacturing model coupled with the computer system, the manufacturing model being capable of generating and modifying at least one control input parameter signal; a machine interface coupled with the manufacturing model, the machine interface being capable of receiving process recipes from the manufacturing model; a processing tool capable of processing semiconductor wafers and coupled with the machine interface, the first processing tool being capable of receiving at least one control input parameter signal from the machine interface; a metrology tool coupled with the first processing tool and the second processing tool, the metrology tool being capable of acquiring metrology data; a film stack optical data reference library, the film stack optical data reference comprising optical data related to a plurality of film stacks; and a film stack data analysis unit coupled to the metrology tool and the film stack optical data reference library, the scatterometry data film stack data analysis unit capable of comparing the metrology data to corresponding data in the film stack optical data reference library and calculating at least one film stack error.

BRIEF DESCRIPTION OF THE DRAWINGS

The invention may be understood by reference to the following description taken in conjunction with the accompanying drawings, in which like reference numerals identify like elements, and in which.

Figure 1:
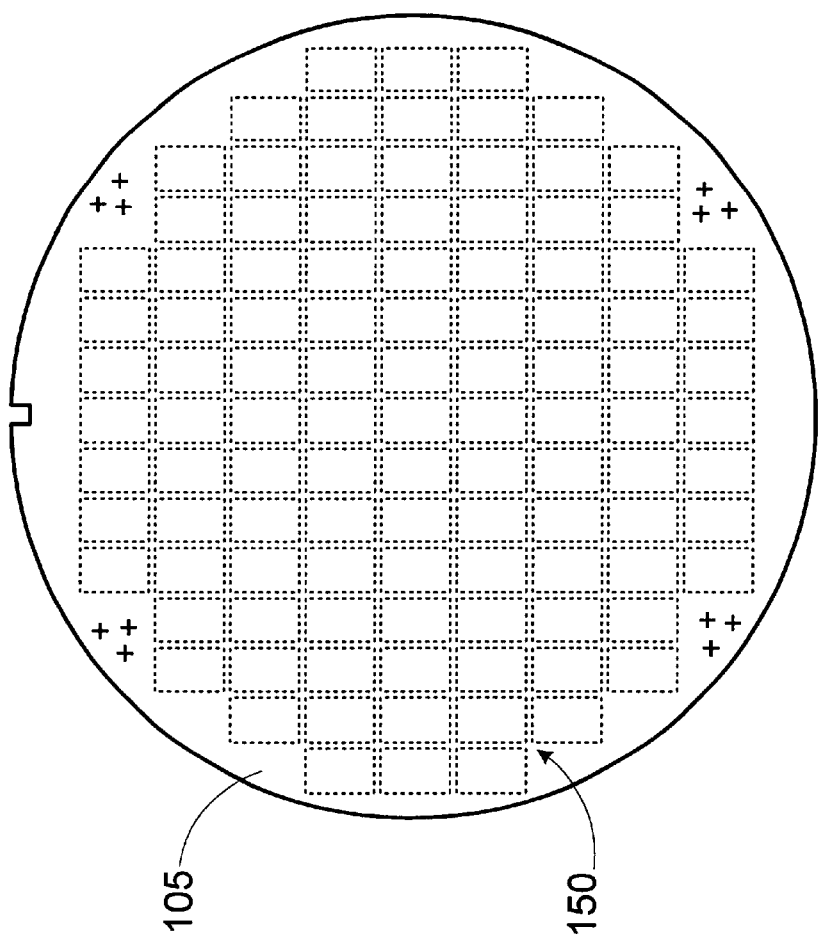
FIG. 1 is a simplified diagram of a prior art semiconductor wafer being processed.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discreet processes that are involved in semiconductor manufacturing. Many times, semiconductor devices are stepped through multiple manufacturing process tools. Errors that can occur during the formation of film stacks on semiconductor wafers being processed can cause significant degradation of the wafers being manufactured. Embodiments of the present invention utilize an optical data acquisition tool, such as a scatterometer, ellipsometer, and the like, to reduce errors during processing of film stack formation on semiconductor wafers. Embodiments of the present invention can also be used to perform fault detection analysis of film stack structures during processing of semiconductor wafers.

Semiconductor devices are processed in a manufacturing environment using a number of input control parameters.

Figure 2:
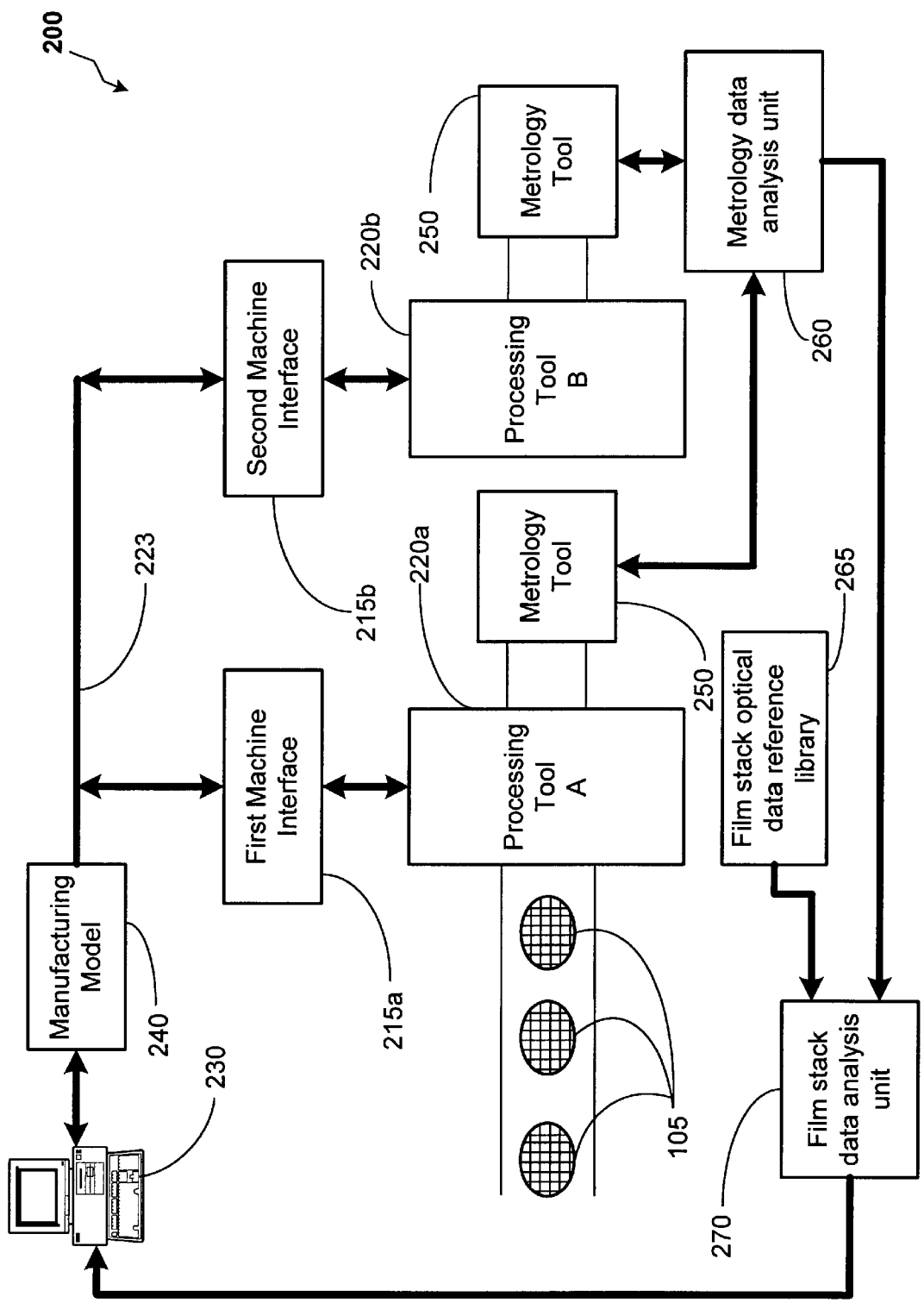
FIG. 2 is a block diagram representation of a system in accordance with one embodiment of the present invention.

Turning now to FIG. 2, a system 200 in accordance with one embodiment of the present invention is illustrated. In one embodiment, semiconductor wafers 105, are processed on processing tools 210a, 210b using a plurality of control input signals, or manufacturing parameters, on a line 223. In one embodiment, control input signals, or manufacturing parameters, on the line 223 are sent to the processing tools 210a, 210b from a computer system 230 via machine interfaces 215a, 215b. In one embodiment, the first and second machine interfaces 215a, 215b are located outside the processing tools 210a, 210b. In an alternative embodiment, the first and second machine interfaces 215a, 215b are located within the processing tools 210a, 210b.

In one embodiment, the computer system 230 sends control input signals, or manufacturing parameters, on the line 223 to the first and second machine interfaces 215a, 215b. The computer system 230 employs a manufacturing model 240 to generate the control input signals on the line 223. In one embodiment, the manufacturing model 240 contains a manufacturing recipe that determines a plurality of control input parameters that are sent on the line 223.

In one embodiment, the manufacturing model 240 defines a process script and input control that implement a particular manufacturing process. The control input signals on the line 223 that are intended for processing tool A 220a are received and processed by the first machine interface 215a. The control input signals on the line 223 that are intended for processing tool B 220b are received and processed by the second machine interface 215b. Examples of the processing tools 220a, 220b used in semiconductor manufacturing processes are steppers, scanners, step-and-scan tools, etch process tools, and the like.

One or more of the semiconductor wafers 105 that are processed by the processing tools 210a, 210b can also be sent to a metrology tool 250 for acquisition of metrology data. The metrology tool 250 can be a scatterometry data acquisition tool, an overlay-error measurement tool, a critical dimension measurement tool, and the like. In one embodiment, one or more processed semiconductor wafers 105 are examined by a metrology tool 250. Data from the metrology tool 250 is collected by a metrology data analyzer unit 260. The metrology data analyzer unit 260 organizes, analyses, and correlates scatterometry metrology data acquired by the metrology tool 250, to particular semiconductor wafers 105 that were examined. The metrology data analyzer unit 260 can be a software unit, a hardware unit, or a firmware unit. In one embodiment, the metrology data analyzer unit 260 is integrated into the computer system 230.

The system 200 comprises a film stack optical data reference library 265. For example, film stack optical data reference libraries are commercially available from Timbre Technologies, Inc. In one embodiment, scatterometry reference library 365 comprises data relating to calculated optical data of a plurality of film stacks that may be formed on semiconductor wafers 105. In an alternative embodiment, the film stack optical data reference library 265 comprises data relating to reflected optical data that occurs in response to optical stimuli engaged upon particular film stack structures on semiconductor wafers 105. A record that contains responses to optical stimuli related to a plurality of film stacks, can be organized and stored into the film stack optical data reference library 265. The stored optical data can be used as reference for comparison of actual wafer data during manufacturing processes.

The particular reflection profile expected for virtually any film stack on a semiconductor wafer 105 depends on the specific characteristics of a film stack and the parameters of the measurement technique employed by the metrology tool 250, such as a scatterometry tool. In general, the scatterometry tool includes optical hardware, such as an ellipsometer or reflectometer, and a data processing unit loaded with a scatterometry software application for processing data collected by the optical hardware. For example, the optical hardware may include a model OP5230 or OP5240 with a spectroscopic ellipsometer offered by Thermawave, Inc. of Freemont, Calif. The data processing unit may comprise a profile application server manufactured by Timbre Technologies, a fully owned subsidiary of Tokyo Electron America, Inc. of Austin, Tex. and distributed by Thermawave, Inc.

The reflection profile for a particular film stack includes the phase and/or intensity of detected light as a function of wavelength or incident angle. The profiles in the film stack optical data reference library 265 are typically calculated theoretically by employing Maxwell's equations based on the expected characteristics and normal process variation of the structures on semiconductor wafers 105. It is also contemplated that profiles in the film stack optical data reference library 265 may be generated empirically by measuring reflection profiles of sample wafers and subsequent characterization of the measured wafers by destructive or non-destructive examination techniques.

A film stack data analysis unit 270 is capable of comparing metrology data from the metrology data acquisition unit 260 to corresponding data from the film stack optical data reference library 265 and characterizing the film stack being analyzed. In one embodiment, the film stack data analysis unit 270 is a software unit that resides within the computer system 230. In an alternative embodiment, the film stack data analysis unit 270 is a hardware unit that is integrated into the system 200. In yet another embodiment, the film stack data analysis unit 270 is a firmware unit integrated within the system 200. The film stack data analysis unit 270 can be used by the system 200 to perform fault analysis of the semiconductor wafers 105 being manufactured, which is described in greater detail below. The film stack data analysis unit 270 can also be used by the system 200 to perform feedback process control, which is described in greater detail below.

Optical metrology data acquisition, such as scatterometry metrology data acquisition is a non-contact semiconductor wafer 105 inspection technique used to acquire metrology data from the semiconductor wafer 105. Scatterometry measurements can be used for particle detection, estimation of particle sizing, critical dimension and profile estimation, film stack characterization, and for roughness measurement of smooth silicon wafer surfaces. Scatterometry measurements are also useful for determining Chemical-Mechanical Polishing (CMP) roughness, and provides for characterization of several film parameters.

Figure 3:
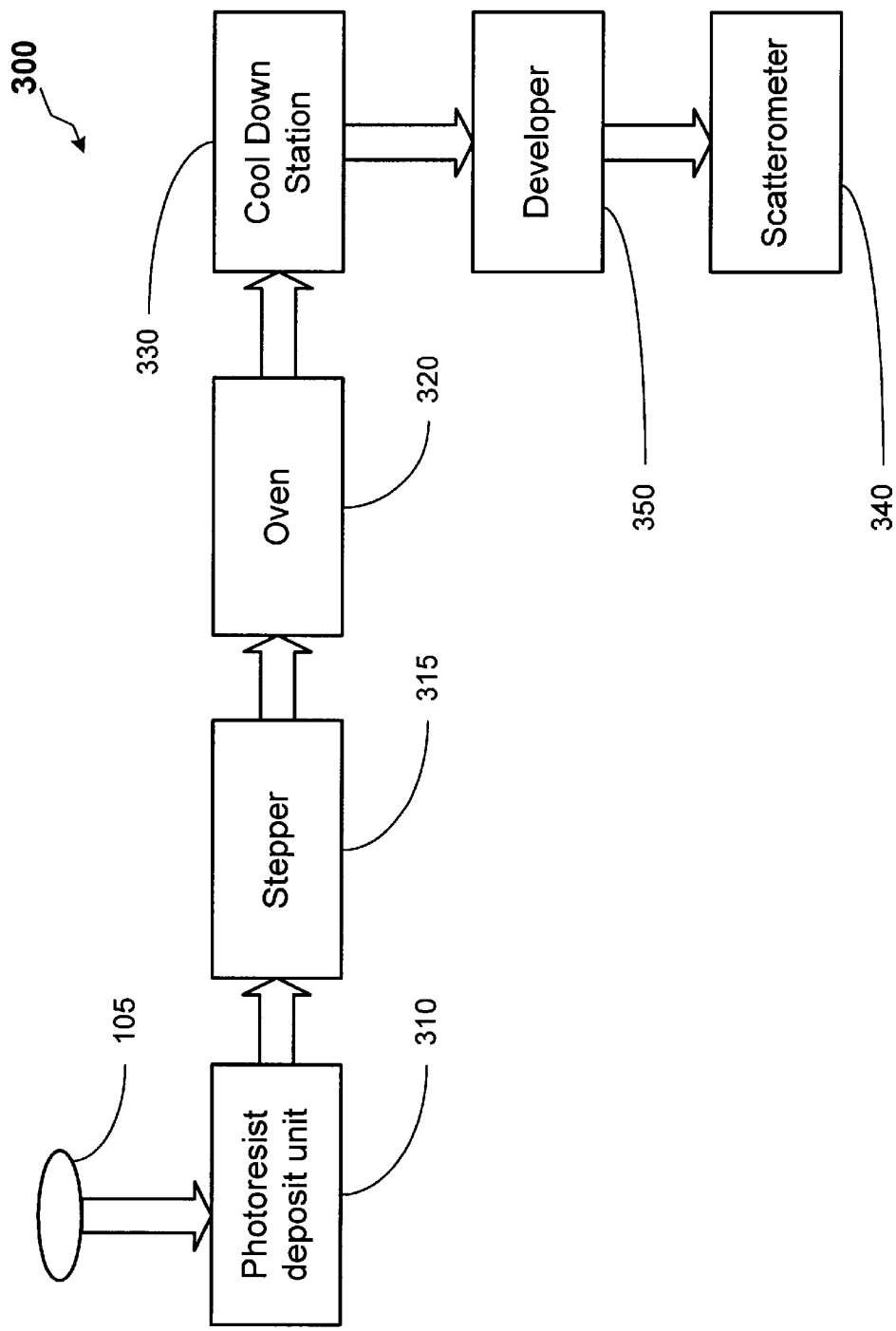
FIG. 3 illustrates one embodiment of a process flow in accordance with one embodiment of the present invention.

Turning now to FIG. 3, one embodiment of an implementation of a scatterometry metrology sequence in the context of semiconductor wafer manufacturing, is illustrated. FIG. 3 shows a simplified diagram of an illustrative processing line 300 for performing photolithography patterning. The processing line 300 includes a photoresist deposition unit 310, a stepper 315, an oven 320, a cool down station 330, a developer 350, and a scatterometer 340. The photoresist deposition unit 310 receives a semiconductor wafer 105, and deposits a predetermined thickness of photoresist material upon the surface of the wafer 105. The stepper 315 then receives the wafer 105 (i.e., or lot of semiconductor wafers) and exposes the wafer 105 to a light source using a reticle to pattern the wafer 105. The wafer 105 is transferred to the oven 320, where a post exposure bake is conducted. Following the post exposure bake, the wafer 105 is transferred to the cool down station 330, and then to the developer 350 after the wafer 105 has sufficiently cooled. The developer 350 removes exposed photoresist material from the wafer 105.

The wafer 105 is then transferred to the scatterometer 340 for measurements. As described in greater detail below, the scatterometer 340 measures the wafer 105 to determine the acceptability and/or uniformity of the previously performed photolithography and etch processes. The computer system 330, which is integrated with the APC framework, based on the wafer measurements, can adjust the recipe of the stepper 315, as needed. As will be recognized by those of ordinary skill in the art in light of this disclosure, the processing line 300 may include discrete or integrated processing tools for performing the processing steps described herein. The data acquired by the scatterometer 340 is used for making modifications to the control input signals on the line 223, which control the processing tools 320.

Figure 4:
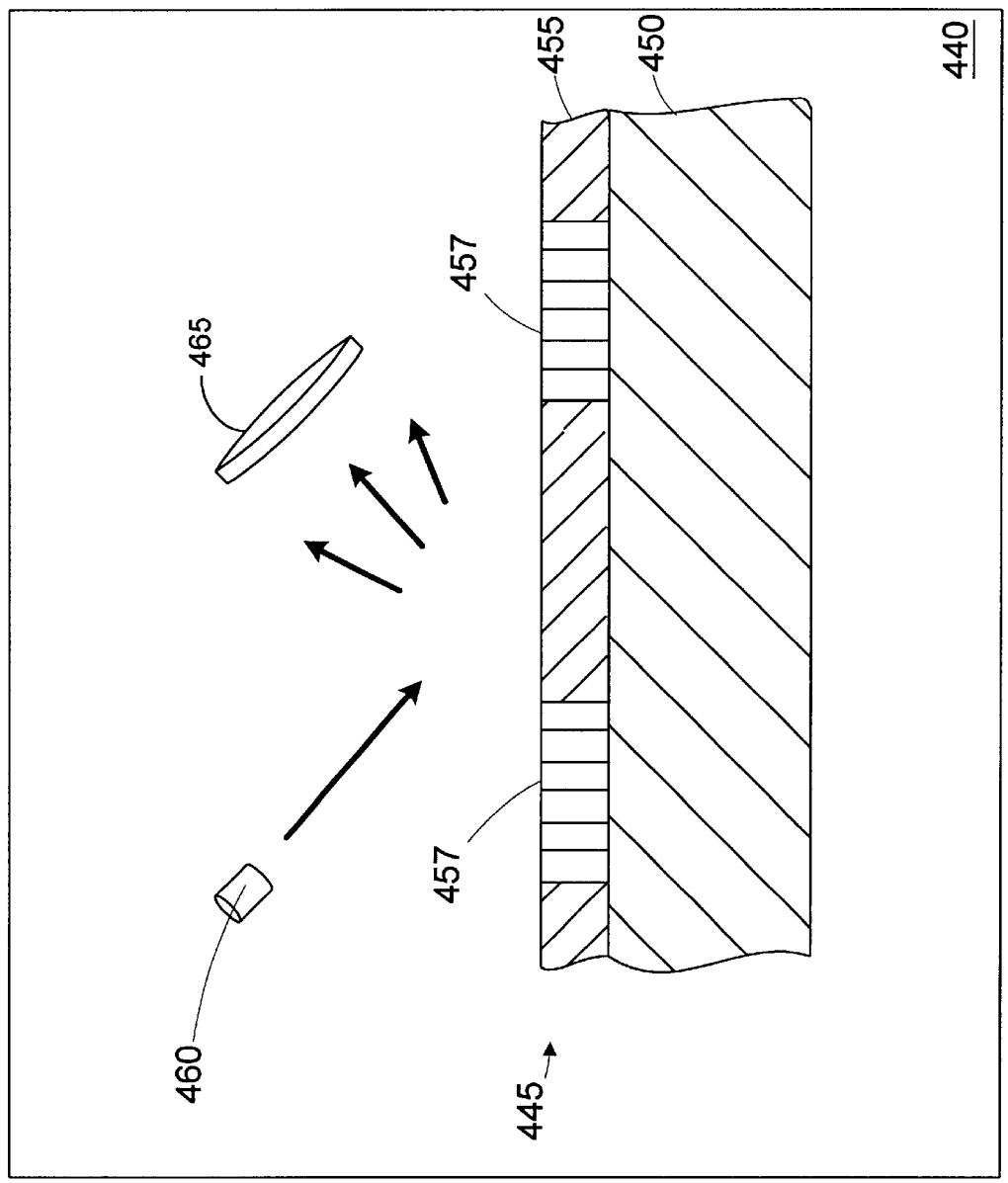
FIG. 4 illustrates a simplified view of a scatterometer with the semiconductor wafer loaded therein.

Referring to FIG. 4, a simplified view of the scatterometer 440 with the wafer 105 loaded therein is provided. The wafer 105 has a base material 450. The photoresist layer 455 has baked regions 457 formed on the base material 450 resulting from the previous exposure and baking steps (i.e., referred to as a patterned wafer 105). The chemical change resulting in the change in solubility of the baked regions 457 also results in the baked regions 457 having an index of refraction different than that of the unexposed portions of the photoresist layer 455.

In one embodiment, the scatterometer 440 comprises a light source 460 and a detector 465 positioned proximate the wafer 105. The light source 460 of the scatterometer 440 illuminates at least a portion of the wafer 105, and the detector 465 takes optical measurements, such as intensity, of the reflected light. Although the invention is described using a scatterometer 440 designed to measure reflected light intensity, it is contemplated that other measurement tools, such as an ellipsometer, a reflectometer, a spectrometer, or some other light-measuring device may be used. It is also contemplated that the scatterometer 440 may use monochromatic light, white light, or some other wavelength or combinations of wave-lengths, depending on the specific implementation. The angle of incidence of the light may also vary, depending on the specific implementation.

The differences in the refractive indices for the baked regions 457 and the unexposed portions of the photoresist layer 455 cause light scattering, resulting in a decrease in the intensity of the reflected light as compared to scattering in the photoresist layer 455 before exposure and baking. The scatterometer 440 measures the intensity at different points on the wafer 105, such as on the periphery and in the middle. A difference in the light intensity, as a function of wavelength or angle, between various points indicates a nonconformity, such as a variation in the line widths of the baked regions 457. The light analyzed by the scatterometer 440 typically includes a reflected component and a scattered component. The reflected component corresponds to the light component where the incident angle equals the reflected angle. The scattered component corresponds to the light component where the incident angle does not equal the reflected angle. For purposes of discussion hereinafter, the term "reflected" light is meant to encompass both the reflected component and the scattered component.

The computer system 330, in conjunction with the manufacturing model 340, adjusts the recipe of the stepper 315 to correct the nonconformity. For example, if the intensity measurement on the periphery of the wafer 105 is greater than the intensity measurement in the middle, the line width is presumably less, because a smaller line width causes less scattering. To correct the line width variation, the computer system 330 changes the recipe of the stepper 315 such that the exposure sites (e.g., individual die) with smaller line widths receive either an increased energy exposure or a longer duration exposure.

In an alternative embodiment, scatterometry measurements can be made before the implementation of the developer process. Detecting variations and adjusting the stepper 315 recipe prior to the developer 350 allows a quicker corrective action response. It is contemplated that all wafers 105 in a lot may be tested, or only selected wafers 105 in the lot. Identifying variations early allows correction of wafers 105 even in the same lot. For more stable steppers 315, the scatterometer 340 may be used only once per shift or once per week, depending on the specific implementation.

In the illustrated embodiment, the photoresist layer 455 is of a chemically-amplified type. In cases where a non-chemically-amplified photoresist material is used, the scatterometer 340 may be stationed prior to the oven 320. In a nonamplified photoresist system, the pattern is essentially complete after exposure in the stepper 315. The post exposure bake in the oven 320, which may be optional, is conducted to smooth the edges in the pattern resulting from standing waves, rather than to complete the patterning. Thus, the exposed portions already have an index of refraction different than the unexposed patterns, and the scatterometer 340 may be used. Scatterometry data is processed and correlated by the system 200. The scatterometry data is then analyzed by the scatterometry error analysis unit 170.

Figure 5:
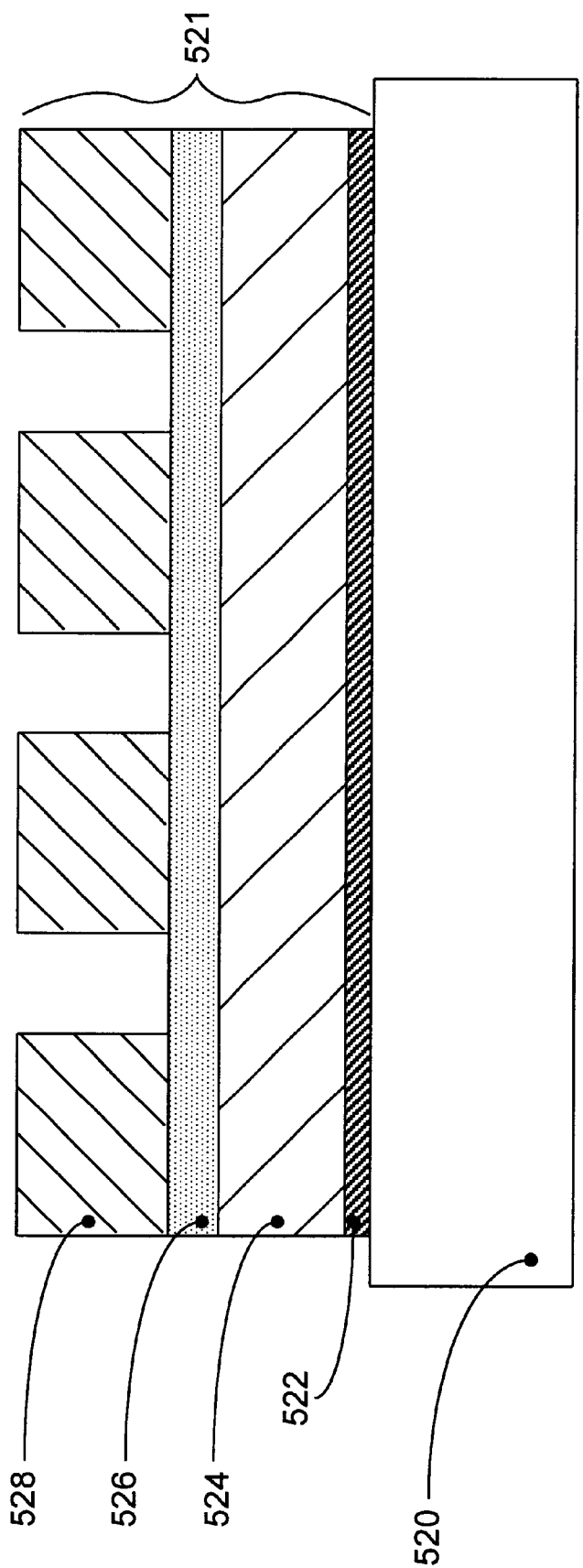
FIG. 5 is a cross-sectional view of an illustrative film stack combination.

Turning now to FIG. 5, an illustrative embodiment of a film stack layer is shown. In one embodiment, a plurality of process layers 522, 524, 526 and 528 are formed above a structure 520 on a semiconductor wafer 105 being processed. The process layers 522, 524, 526 and 528 are arranged to form a film stack 521. The film stack 521 is generally subjected to a plurality of semiconductor manufacturing processing operations by the system 200. In the embodiment illustrated in FIG. 5, the process layer 522 is comprised of silicon dioxide, the process layer 524 is comprised of polysilicon, the process layer 526 is comprised of an anti-reflective coating ("ARC") material, and the process layer 528 is a patterned layer of photoresist. In one embodiment, the structure 520 is a semiconducting substrate, such as a silicon wafer. In an alternative embodiment, the structure 520 may represent one or more previously formed layers of material on a semiconductor wafer 105. One example of a previously formed layer represented by the structure 520 is a stack of insulating layers each having a plurality of conductive interconnections formed therein.

The various process layers that form the film stack 521 depicted in FIG. 5 may be formed by a variety of techniques, and may be made from a variety of materials. For example, the layer of silicon dioxide comprising the process layer 522 may be formed by a thermal growth process in a wet or dry furnace, and it may have a thickness ranging from approximately 2–5 nm (20–50 Å). The polysilicon material comprising the process layer 524 may be either undoped or doped with an appropriate dopant material, e.g., arsenic, boron, and it may be formed by a deposition process to a thickness ranging from approximately 150–300 nm (1500–3000 Å). The process layer 526 may be comprised of a variety of anti-reflective coating materials, e.g., silicon nitride (SiN), silicon oxynitride (SiON), and it may be formed by a deposition process to a thickness ranging from approximately 30–50 nm (300–500 Å). The process layer 528 may be comprised of either a positive or negative type photoresist, and it may have a thickness ranging from approximately 400–1000 nm (4,000–10,000 Å).

The above described variations in the various process layers 522, 524, 526, 528 may result in a variety of possible or probable film stacks 521 combinations. Each of these film stack 521 combinations may exhibit a unique optical characteristic trace due to the variation in the values of reflectivity, index of refraction ("n") and extinction coefficient ("k") of the various process layers comprising the film stack 521. Such variations may be due to thickness variations, material variation and/or methods of manufacture.

Embodiments of the present invention provide for generating a library (i.e., the film stack optical data reference library 265) containing optical characteristic traces for a plurality of film stack 521 combinations that may be encountered in the semiconductor manufacturing facility. In turn, the film stack optical data reference library 265 can be used to determine, characterize, perform fault detection, distinguish and/or confirm the composition of the film stack 521 that is to be subjected to subsequent processing operations, for example, an etching process, or other types of semiconductor manufacturing processes. The film stack optical data reference library 265 can also be used to perform fault detection analysis of film stacks on the semiconductor wafers 105.

Figure 6:
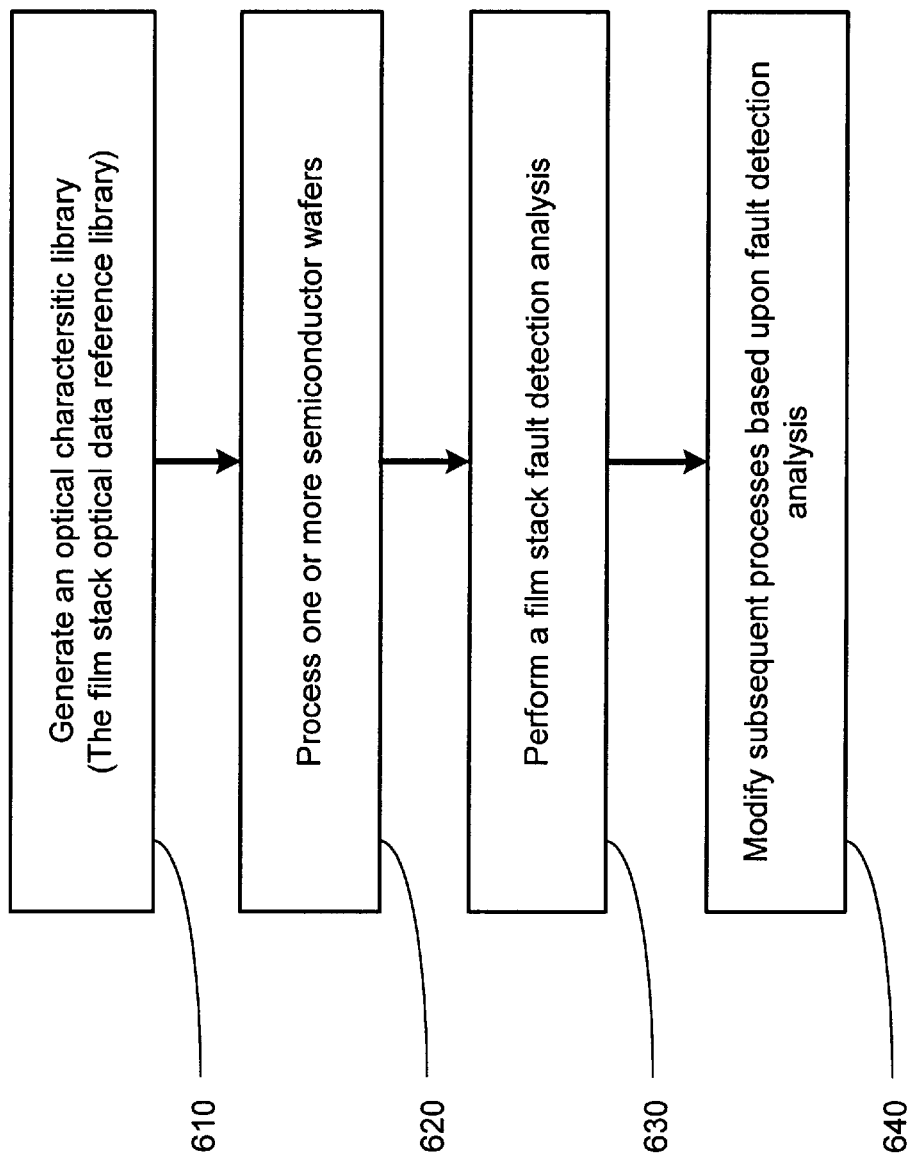
FIG. 6 illustrates a flowchart depiction of a method in accordance with one embodiment of the present invention.

Turning now to FIG. 6, a flowchart depiction of the methods in accordance with one embodiment of the present invention is illustrated. The system 200 generates a film stack optical data reference library 265 to be used as a reference for performing fault detection (block 610). The system 200 uses the film stack optical data reference library 265, to characterized film stack characteristics of film stacks being processed on semiconductor wafers 105. A more detailed description of generating a film stack optical data reference library 265 is described below. Once the system 200 generates a film stack optical data reference library 265, the system 200 performs processing of semiconductor wafers 105 (block 620).

The system 200 then performs a film stack fault detection analysis upon the semiconductor wafers 105 being processed (block 630). The film stack fault detection analysis yields errors that may be present in the film stack on the semiconductor wafers 105 being processed. The system 200 can analyze the errors discovered on the semiconductor wafers 105 and perform corrective measures. When a film stack fault is detected, the system 200 can classify the fault using data from the film stack optical data reference library 265. The classification of the film stack fault can reduce the time period required to diagnose the cause of the fault.

In one embodiment, the system 200 modifies subsequent semiconductor manufacturing processes based upon the data received from the fault detection analysis (block 640). Modifications to subsequent manufacturing processes are made by the system 200 to reduce the possibilities of subsequent errors occurring in the semiconductor wafers 105 being processed. Modifications made to subsequent manufacturing processes are also made in order to reduce the effects of the errors detected during the film stack fault detection analysis performed by the system 200.

Figure 7:
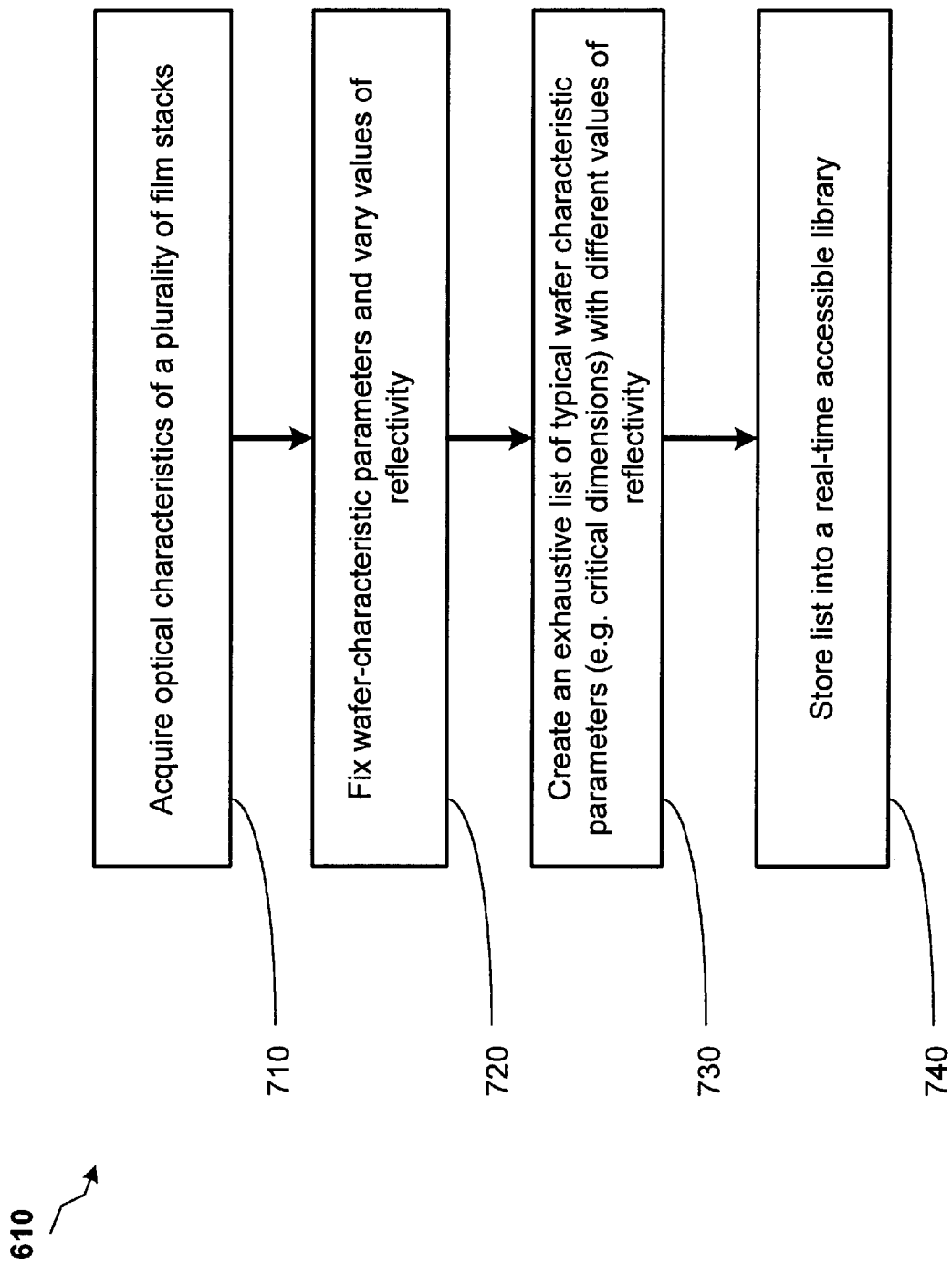
FIG. 7 illustrates a flowchart depiction of a method of generating an optical characteristic library described in FIG. 5, in accordance with one embodiment of the present invention.

Turning now to FIG. 7, a flowchart depiction of the steps for generating a film stack optical data reference library 265, as indicated in block 610 of FIG. 6, in accordance with one embodiment of the present invention, is illustrated. The system 200 acquires optical characteristics of a plurality of film stacks (block 710). Optical characterization techniques, such as scatterometry techniques, can be used to characterize process layers in a film stack. Optical characteristics in the process layers in a film stack, can be measured using optical characteristic data acquisition tools such as a scatterometer, an elipsometer, a reflectometer, or the like. Those skilled in the art who have benefit of the present disclosure can define a relationship between film stack device structures; such as the thickness of process layers, the index of the fraction, n, the dielectric constant, k, associated with a film stack; the critical dimensions on formations on a semiconductor wafer 105; and the like; with optical characteristics detected by a optical data acquisition tool. Therefore, a set of data that relates particular physical characteristics, such as film stack characteristics, on a semiconductor wafer 105 with certain optical characteristics, such as the magnitude, the phase, and the angle of reflective light, can be correlated to generate the film stack optical data reference library 265.

The film stack optical data reference library 265 can be created such that a look up feature can be used to consult the film stack optical data reference library 265 to perform data comparisons. Optical characteristics of film stacks can also be acquired by other testing means, such as slicing a sample wafer 105 and studying the characteristics of a film stack on the sliced semiconductor wafer 105 and comparing it to optical characteristics data received from analysis of the sample semiconductor wafer 105. Other types of destructive and non-destructive tests known by those skilled in the art can be used to acquire optical characteristics of film stacks.

The system 200 then fixes certain wafer 105 characterization parameters, and varies optical characteristics, such as the index of refraction and dielectric coefficients (block 720). By fixing certain wafer 105 characteristics parameters, such as the critical dimension measurements, thickness of profile elements of a film stack, and the like, and correlating them with a plurality of optical characteristics such as n and k, an exhaustive list of typical wafer 105 characteristic parameters can be generated (block 730). This exhaustive list, which contains a plurality of sets of wafer characteristic parameters that are held constant while a plurality of optical characteristics, such as n and k are varied, is stored into a database (block 740). The exhaustive lists are stored into a database such that the lists can be accessed in real time. In one embodiment, these exhaustive lists are stored into the film stack optical data reference library 265. The completion of the steps described in FIG. 7, substantially completes the step of generating an optical characteristics library described in block 610 of FIG. 6.

Figure 8:
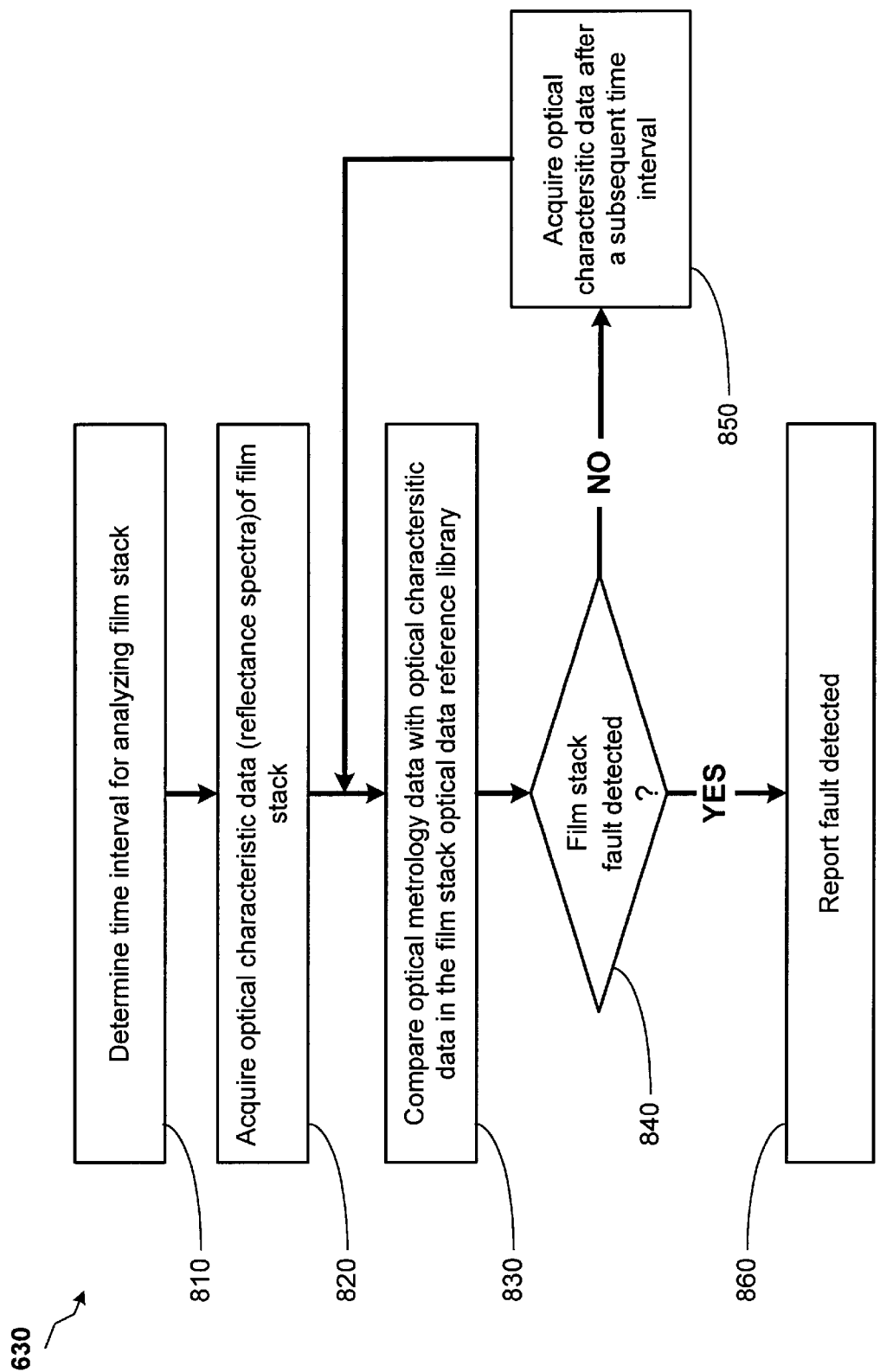
FIG. 8 illustrates a flowchart depiction of a method of performing film stack fault detection analysis described in FIG. 5, in accordance with one embodiment of the present invention.

Turning now to FIG. 8, a flowchart depiction of one embodiment of performing the film stack fault detection analysis described in block 630 of FIG. 6, is illustrated. The system 200 predetermines a time interval for analyzing the film stack of certain semiconductor wafers 105 being processed (block 810). The determination of the time interval in generally based upon the type of film stack being processed and the rate of semiconductor wafers 105 being encountered with significant amount of errors. The appropriate time interval between film stack analyses can be determined by those skilled in the art who have the benefit of the present disclosure.

Once a time interval for analyzing the film stack on a semiconductor wafer 105 is determined, the system 200 acquires optical characteristic data relating to the film stack at the appropriate, predetermined time intervals (block 820).

In one embodiment, optical characteristic data (e.g., the reflectance spectra of the film stack) is acquired by the metrology tool 150, which in one embodiment is a scatterometry tool. The system 200 uses the optical characteristic data acquired by the metrology tool 150 and characterizes certain wafer 105 characteristic parameters, such as critical dimensions and film thicknesses, associated with the film stack. The optical characteristics of the film stack can indicate a plurality of possible problems associated with the film stack, such as excursions, and the like. Optical film stack characteristic data analysis can also be used to detect faults resulting from particular settings of deposition chambers, gas chambers, and the like.

The system 200 compares the metrology optical characteristic data with optical characteristic data in the film stack optical data reference library 265 (block 830). The system 200 uses a fixed wafer 105 characteristic parameter, such a fixed critical dimension value, and scans across a plurality of table values that corresponds to the particular wafer 105 characteristic data.

Some of the entries that are associated with a particular critical dimension, but contain a plurality of optical characteristics associated with that particular wafer 105 characteristic, define a possible fault in the film stack. In other words, a particular wafer 105 characteristic may be associated with a plurality of optical characteristics, some of which may define a possible fault in the film stack. In order to find possible faults in the film stacks, the system 200 uses the fixed wafer 105 characteristic values to scan across a plurality of table entries that contains optical characteristics associated with the particular wafer 105 characteristics.

The system 200 then determines whether the film stack contains a fault based upon the table value cited by the comparison of the optical characteristic measured with the optical characteristic stored in the library (block 840). When the system 200 determines that the acquired optical characteristic data associated with the film stack does not contain a fault as indicated by the table entry in the film stack optical data reference library 265, the system 200 awaits the next time period after the predetermined interval to acquire optical characteristic data for the next film stack (block 850). When the system 200 determines that the film stack under analysis make contains a possible fault, the fault, as defined by the table entries in the film stack optical data reference library 265, is reported (block 860). The completion of the steps described in FIG. 8, substantially completes the step of performing the film stack fault detection analysis indicated in block 630 of FIG. 6.

Figure 9:
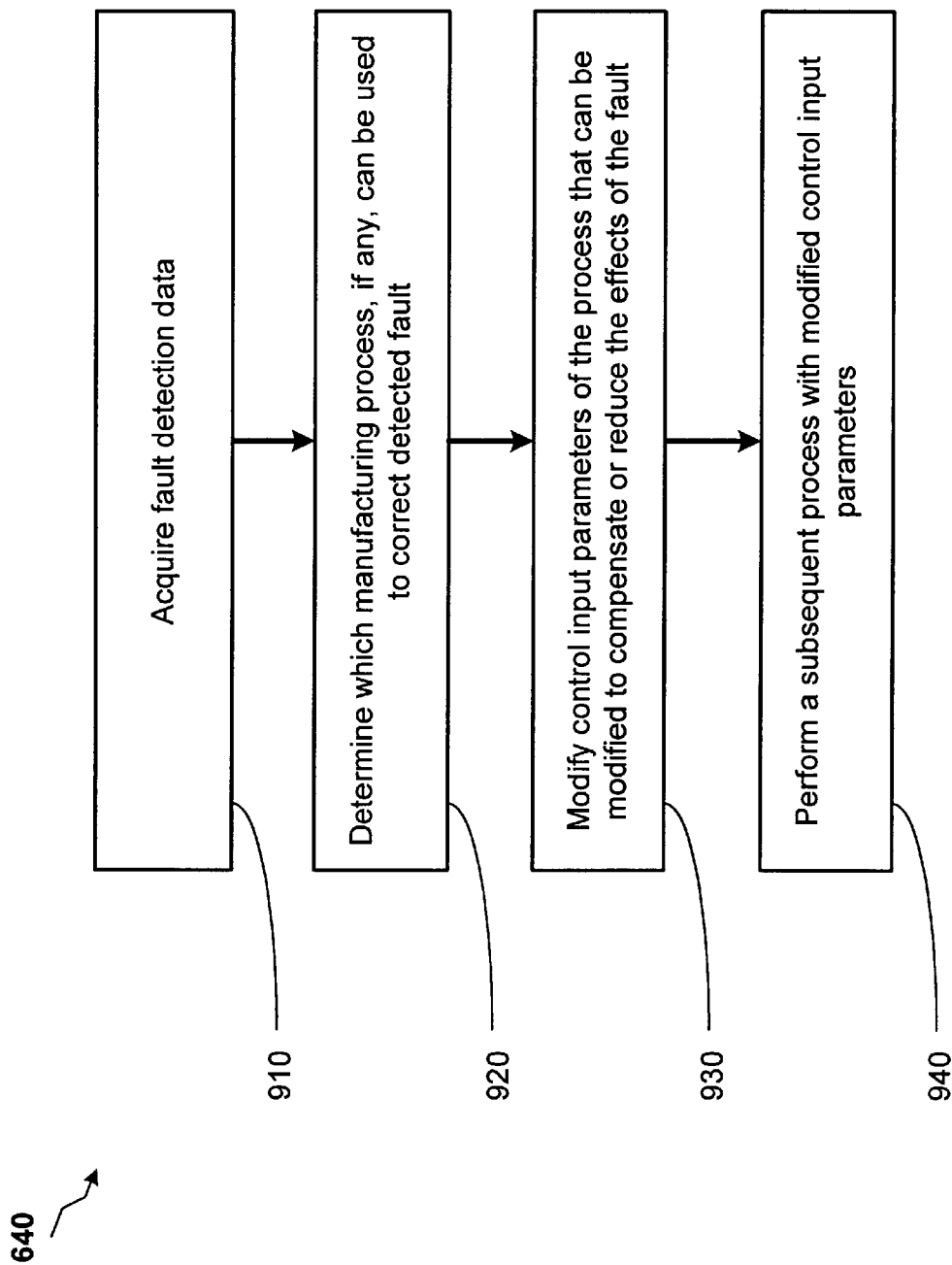
FIG. 9 illustrates a flowchart depiction of a method of performing a modification of a subsequent process based upon fault detection analysis described in FIG. 5, in accordance with one embodiment of the present invention.

Turning now to FIG. 9, a flowchart depiction of performing the modification of subsequent processes based upon the fault detection analysis, indicated in block 640 of FIG. 6, in accordance with one embodiment of the present invention, is illustrated. In order to perform modifications to subsequent manufacturing processes, the system 200 acquires fault detection data based upon the fault detection analysis (block 910). The fault detection data, which indicates errors within particular process layers in the film stack, is analyzed in order to determine whether a process being performed on a semiconductor wafer 105 can be modified to correct or to compensate for the error (block 920). Those skilled in the art and have the benefit of the present disclosure can analyze the error data received from the fault detection analysis and determine a manufacturing process that may be modified to compensate for the error.

The system 200 then modifies control input parameters from processing tools 220 that perform the manufacturing processes that are to be modified (block 930). In one embodiment, processing tools 220, such as a thin film process tool, can be adjusted in order to affect the optical characterization of the film stack such that an optical characterization of the film stack falls within an acceptable predetermined specification. Furthermore, processing tools 220, such as deposition process tools, can be modified to affect process layers in the film stack such that the resulting optical characteristics associated with the optical analysis of the film stack contains parameters that fall within a predetermined acceptable specification. Once the control input parameters for modifying manufacturing process is determined, subsequent processing of semiconductor wafers 105 is performed based upon the modified control input parameters (block 940). The principals taught by the present invention can be implemented in an in-line matter during the processing of semiconductor wafers 105. Therefore, substantially real time corrections to films stacks can be performed utilizing the principals taught by embodiments of the present invention.

The principles taught by the present invention can be implemented in an Advanced Process Control (APC) Framework. The APC is a preferred platform from which to implement the control strategy taught by the present invention. In some embodiments, the APC can be a factory-wide software system, therefore, the control strategies taught by the present invention can be applied to virtually any of the semiconductor manufacturing tools on the factory floor. The APC framework also allows for remote access and monitoring of the process performance. Furthermore, by utilizing the APC framework, data storage can be more convenient, more flexible, and less expensive than local drives. The APC platform allows for more sophisticated types of control because it provides a significant amount of flexibility in writing the necessary software code.

Deployment of the control strategy taught by the present invention onto the APC framework could require a number of software components. In addition to components within the APC framework, a computer script is written for each of the semiconductor manufacturing tools involved in the control system. When a semiconductor manufacturing tool in the control system is started in the semiconductor manufacturing fab, it generally calls upon a script to initiate the action that is required by the process controller, such as the overlay controller. The control methods are generally defined and performed in these scripts. The development of these scripts can comprise a significant portion of the development of a control system. The principles taught by the present invention can be implemented into other types of manufacturing frameworks.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:

processing at least one semiconductor wafer;

acquiring metrology data from said processed semiconductor wafer;

accessing data from a reference library comprising optical data relating to a film stack on said semiconductor wafer;

comparing said metrology data to data from said reference library; and performing a fault-detection analysis in response to said comparison of said metrology data and said reference library data.

2. The method described in claim 1, further comprising generating said reference library that comprises optical signature data relating to characteristics of a plurality of film stacks on a semiconductor wafer.

3. The method described in claim 2, wherein generating said reference library that comprises optical signature data relating to characteristics of a plurality of film stacks comprises:

determining an optical characteristic trace for a plurality of probable film stack combinations;

creating a table comprising said optical characteristic trace; and storing said table.

4. The method described in claim 3, wherein creating a table comprises varying at least one optical characteristic of said film stack with corresponding film stack characteristics.

5. The method described in claim 4, wherein varying at least one optical characteristic comprises varying an index of refraction associated with said film stack.

6. The method described in claim 1, wherein processing at least one semiconductor wafer comprises performing a photolithography process on said semiconductor wafer.

7. The method described in claim 3, wherein processing at least one semiconductor wafer further comprises performing an etch process on said semiconductor wafer.

8. The method described in claim 2, wherein accessing data from a reference library comprising optical data relating to a film stack comprises accessing data from a reference library comprising optical data relating to a film stack that comprises of at least one of a layer of metal, a layer of polysilicon, a layer of silicon dioxide, a layer of silicon nitride, a layer of silicon oxynitride, and a layer of photoresist material.

9. The method described in claim 8, wherein comparing said metrology data to data from said reference library comprises comparing metrology data related to a film stack to said data from said reference library.

10. The method described in claim 9, wherein comparing metrology data related to a film stack comprises comparing metrology data related to a film stack that comprises at least one of a layer of metal, a layer of polysilicon, a layer of silicon dioxide, a layer of silicon nitride, a layer of silicon oxynitride, and a layer of photoresist material.

11. The method described in claim 2, wherein acquiring metrology data from said processed semiconductor wafer comprises:

illuminating at least a portion of said film stack; and measuring reflected light resulting from said illumination to generate an optical signature of said film stack.

12. The method described in claim 2, wherein acquiring metrology data from said processed semiconductor wafer further comprises performing scatterometry data acquisition.

13. The method described in claim 2, wherein performing a fault-detection analysis in response to said comparison of said metrology data and said reference library data comprises:

determining a reflectance spectra of said film stack;

determining if said reflectance spectra of said film stack produces an optical characteristic that substantially correlates with a predetermined optical characteristic stored in said reference library; and determining that a film stack error exists based upon a determination that said composition of said film stack does not substantially correlate with said predetermined optical characteristic stored in said reference library.

14. The method described in claim 13, further comprising performing a process control compensation in response to said comparison of said metrology data and said reference library data.

15. The method described in claim 14, wherein comprising performing a process control compensation in response to said comparison of said metrology data and said reference library data comprises modifying at least one control parameter in response to said comparison of said metrology data and said reference library data.

16. The method described in claim 14, wherein performing a fault-detection analysis in response to said comparison of said metrology data and said reference library data further comprises flagging a fault with said metrology data does not properly match a corresponding data in said reference library.

17. A method, comprising:

processing at least one semiconductor wafer;

generating a reference library, said reference library comprising a plurality of optical data relating to a plurality of film stacks on said semiconductor wafer;

illuminating at least a portion of a film stack on said semiconductor wafer;

measuring reflected light resulting from said illumination to generate an optical signature of said film stack;

comparing said measured reflected light related to said film stack with corresponding optical data from said reference library; and performing at least one of a fault-detection analysis and a process control compensation in response to said comparison of said measured reflected light and said optical data from said reference library.

18. The method described in claim 17, wherein illuminating at least a portion of a film stack comprises illuminating a film stack that comprises of at least one of a layer of metal, a layer of polysilicon, a layer of silicon dioxide, a layer of silicon nitride, a layer of silicon oxynitride, and a layer of photoresist material.

19. The method described in claim 18, wherein measuring reflected light resulting from said illumination to generate an optical signature of said film stack comprises performing scatterometry data acquisition.

20. The method described in claim 19, wherein performing a fault-detection analysis in response to said comparison of said metrology data and said reference library data comprises:

determining a composition of said film stack;

determining if said composition of said film stack produces an optical characteristic that substantially correlates with a predetermined optical characteristic stored in said reference library; and determining that a film stack error exists based upon a determination that said composition of said film stack does not substantially correlate with said predetermined optical characteristic stored in said reference library.

21. The method described in claim 20, further comprising performing a process control compensation in response to said comparison of said metrology data and said reference library data.

22. The method described in claim 21, wherein comprising performing a process control compensation in response to said comparison of said metrology data and said reference library data comprises modifying at least one control parameter in response to said comparison of said metrology data and said reference library data.

23. A system, comprising:

a computer system;

a manufacturing model coupled with said computer system, said manufacturing model being capable of generating and modifying at least one control input parameter signal;

a machine interface coupled with said manufacturing model, said machine interface being capable of receiving process recipes from said manufacturing model;

a processing tool capable of processing semiconductor wafers and coupled with said machine interface, said first processing tool being capable of receiving at least one control input parameter signal from said machine interface;

a metrology tool coupled with said first processing tool and said second processing tool, said metrology tool being capable of acquiring metrology data;

a film stack optical data reference library, said film stack optical data reference comprising optical data related to a plurality of film stacks; and a film stack data analysis unit coupled to said metrology tool and said film stack optical data reference library, said scatterometry data film stack data analysis unit capable of comparing said metrology data to corresponding data in said film stack optical data reference library and calculating at least one film stack error.

24. The system of claim 23, wherein said computer system is capable of generating modification data for modifying at least one control input parameter in response to said calculation of said film stack error.

25. The system of claim 24, wherein said manufacturing model is capable of modifying said control input parameter in response to said modification data.

26. An apparatus, comprising:

means for processing at least one semiconductor wafer;

means for acquiring metrology data from said processed semiconductor wafer;

means for accessing data from a reference library comprising optical data relating to a film stack on said semiconductor wafer;

means for comparing said metrology data to data from said reference library; and means for performing a fault-detection analysis in response to said comparison of said metrology data and said reference library data.

27. A computer readable program storage device encoded with instructions that, when executed by at least one computer, performs a method, comprising:

processing at least one semiconductor wafer;

acquiring metrology data from said processed semiconductor wafer;

accessing data from a reference library comprising optical data relating to a film stack on said semiconductor wafer;

comparing said metrology data to data from said reference library; and performing a fault-detection analysis in response to said comparison of said metrology data and said reference library data.

28. The computer readable program storage device encoded with instructions that, when executed by a computer, performs the method described in claim 27, further comprising generating said reference library that comprises optical signature data relating to characteristics of a plurality of film stacks on a semiconductor wafer.

29. The computer readable program storage device encoded with instructions that, when executed by a computer, performs the method described in claim 28, wherein generating said reference library that comprises optical signature data relating to characteristics of a plurality of film stacks comprises:

determining an optical characteristic trace for a plurality of probable film stack combinations;

creating a table comprising said optical characteristic trace; and storing said optical characteristic trace.

30. The computer readable program storage device encoded with instructions that, when executed by a computer, performs the method described in claim 29, wherein creating a table comprises varying at least one optical characteristic of said film stack with corresponding film stack characteristics.

31. The computer readable program storage device encoded with instructions that, when executed by a computer, performs the method described in claim 30, wherein varying at least one optical characteristic comprises varying an index of refraction associated with said film stack.

32. The computer readable program storage device encoded with instructions that, when executed by a computer, performs the method described in claim 30, wherein varying at least one optical characteristic comprises varying an index of refraction associated with said film stack.

33. The computer readable program storage device encoded with instructions that, when executed by a computer, performs the method described in claim 27, wherein processing at least one semiconductor wafer comprises performing a photolithography process on said semiconductor wafer.

34. The computer readable program storage device encoded with instructions that, when executed by a computer, performs the method described in claim 29, wherein processing at least one semiconductor wafer further comprises performing an etch process on said semiconductor wafer.

35. The computer readable program storage device encoded with instructions that, when executed by a computer, performs the method described in claim 28, wherein accessing data from a reference library comprising optical data relating to a film stack comprises accessing data from a reference library comprising optical data relating to a film stack that comprises of at least one of a layer of metal, a layer of polysilicon, a layer of silicon dioxide, a layer of silicon nitride, a layer of silicon oxynitride, and a layer of photoresist material.

36. The computer readable program storage device encoded with instructions that, when executed by a computer, performs the method described in claim 35, wherein comparing said metrology data to data from said reference library comprises comparing metrology data related to a film stack to said data from said reference library.

37. The computer readable program storage device encoded with instructions that, when executed by a computer, performs the method described in claim 36, wherein comparing metrology data related to a film stack comprises comparing metrology data related to a film stack that comprises at least one of a layer of metal, a layer of polysilicon, a layer of silicon dioxide, a layer of silicon nitride, a layer of silicon oxynitride, and a layer of photoresist material.

38. The computer readable program storage device encoded with instructions that, when executed by a computer, performs the method described in claim 28, wherein acquiring metrology data from said processed semiconductor wafer comprises:

illuminating at least a portion of said film stack; and measuring reflected light resulting from said illumination to generate an optical signature of said film stack.

39. The computer readable program storage device encoded with instructions that, when executed by a computer, performs the method described in claim 28, wherein acquiring metrology data from said processed semiconductor wafer further comprises performing scatterometry data acquisition.

40. The computer readable program storage device encoded with instructions that, when executed by a computer, performs the method described in claim 28, wherein performing a fault-detection analysis in response to said comparison of said metrology data and said reference library data comprises:

determining a reflectance spectra of said film stack;

determining if said reflectance spectra of said film stack produces an optical characteristic that substantially correlates with a predetermined optical characteristic stored in said reference library; and determining that a film stack error exists based upon a determination that said composition of said film stack does not substantially correlate with said predetermined optical characteristic stored in said reference library.

41. The computer readable program storage device encoded with instructions that, when executed by a computer, performs the method described in claim 40, further comprising performing a process control compensation in response to said comparison of said metrology data and said reference library data.

42. The computer readable program storage device encoded with instructions that, when executed by a computer, performs the method described in claim 35, wherein comprising performing a process control compensation in response to said comparison of said metrology data and said reference library data comprises modifying at least one control parameter in response to said comparison of said metrology data and said reference library data.

43. The computer readable program storage device encoded with instructions that, when executed by a computer, performs the method described in claim 28, wherein performing a fault-detection analysis in response to said comparison of said metrology data and said reference library data further comprises flagging a fault with said metrology data does not properly match a corresponding data in said reference library.

* * * * *